US010933010B2

(12) United States Patent
Taniguchi et al.

(10) Patent No.: US 10,933,010 B2
(45) Date of Patent: Mar. 2, 2021

(54) EXTERNAL DERMAL AGENT

(71) Applicant: Hayashibara Co., Ltd., Okayama (JP)

(72) Inventors: Mutsuko Taniguchi, Okayama (JP); Go Takikawa, Okayama (JP); Kiyomi Aizawa, Okayama (JP); Tatsuya Ishihara, Okayama (JP)

(73) Assignee: Hayashibara Co., Ltd., Okayama (JP)

( * ) Notice: Subject to any disclaimer, the term of this patent is extended or adjusted under 35 U.S.C. 154(b) by 80 days.

(21) Appl. No.: 15/572,205

(22) PCT Filed: Apr. 26, 2016

(86) PCT No.: PCT/JP2016/063078
§ 371 (c)(1),
(2) Date: Nov. 7, 2017

(87) PCT Pub. No.: WO2016/181828
PCT Pub. Date: Nov. 17, 2016

(65) Prior Publication Data
US 2018/0116940 A1 May 3, 2018

(30) Foreign Application Priority Data
May 11, 2015 (JP) .............................. JP2015-096839

(51) Int. Cl.
A61K 8/73 (2006.01)
A61Q 19/00 (2006.01)
A61K 8/39 (2006.01)
A61K 8/81 (2006.01)
A61Q 19/08 (2006.01)

(52) U.S. Cl.
CPC .................. A61K 8/73 (2013.01); A61K 8/39 (2013.01); A61K 8/8152 (2013.01); A61Q 19/00 (2013.01); A61Q 19/08 (2013.01); A61K 2800/546 (2013.01)

(58) Field of Classification Search
None
See application file for complete search history.

(56) References Cited

U.S. PATENT DOCUMENTS

| 2003/0082221 A1* | 5/2003 | O'Halloran | A61K 8/0208 424/401 |
| 2006/0257346 A1* | 11/2006 | Mohammadi | A61K 8/25 424/70.12 |
| 2009/0041814 A1 | 2/2009 | Nanbu | |
| 2014/0234426 A1* | 8/2014 | Kasagi | A61K 8/0241 424/489 |

FOREIGN PATENT DOCUMENTS

| EP | 1563831 A1 | 8/2005 |
| EP | 1878421 A1 | 1/2008 |
| EP | 2868701 A1 | 5/2015 |
| FR | 2994387 A1 | 2/2014 |
| JP | 1988-139105 A | 6/1988 |
| JP | 1993933 A | 1/1993 |
| JP | 11180823 A | 7/1999 |
| JP | 2001-72547 A | 3/2001 |
| JP | 2009-40697 A1 | 2/2009 |
| JP | 2010-001239 A | 1/2010 |
| JP | 4590186 B2 | 12/2010 |
| JP | 2011-219424 A | 11/2011 |
| JP | 2012-36176 A | 2/2012 |
| JP | 2012-206956 A | 10/2012 |
| JP | 2014-91710 A | 5/2014 |
| JP | 2015-007007 A | 1/2015 |
| WO | 03/026583 A2 | 4/2003 |
| WO | 2005067884 A1 | 7/2005 |
| WO | 2012008457 A1 | 1/2012 |

* cited by examiner

Primary Examiner — Robert A Wax
Assistant Examiner — Randeep Singh
(74) Attorney, Agent, or Firm — Browdy and Neimark, PLLC

(57) ABSTRACT

[Object]
The present invention aims to provide an external dermal agent that tightens the skin, lifts up sagging skin, has no stickiness to the skin, and has a satisfactory compatibility with the skin, without giving any unfavorable feeling to users.
[Means to Attain the Object]
The present invention solves the above object by providing an external dermal agent characterized in that it contains pullulan and an alkaline-swelling polymer in a mass ratio of the pullulan to the alkaline-swelling polymer being 10 or more.

10 Claims, 1 Drawing Sheet

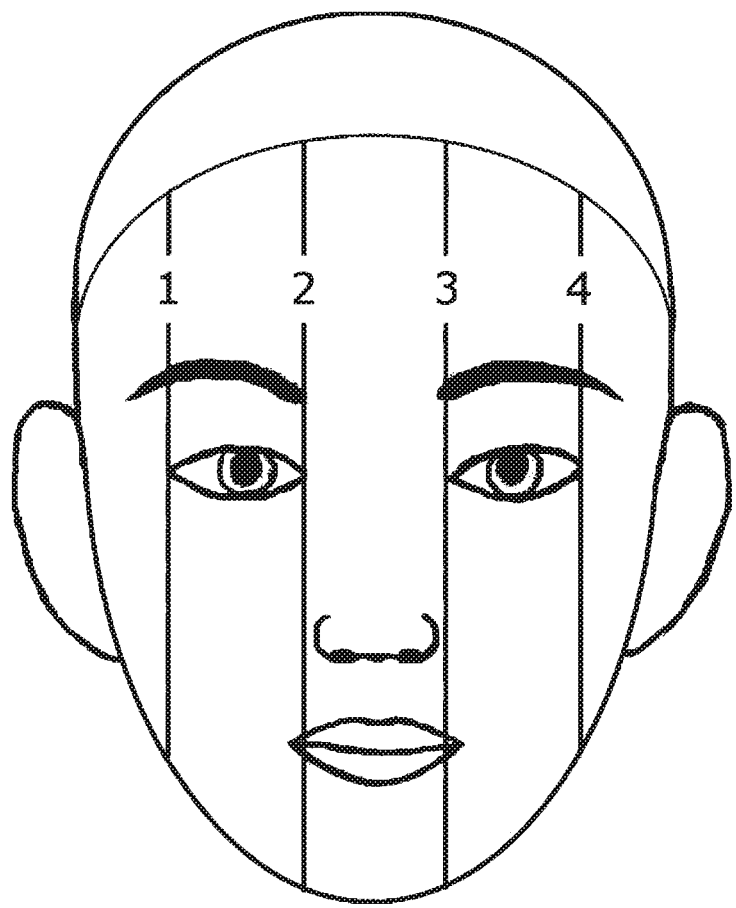

EXTERNAL DERMAL AGENT

TECHNICAL FIELD

The present invention relates to an external dermal agent, and more particularly, to an external dermal agent having an action of tightening the skin and lifting up sagging skin.

BACKGROUND ART

To keep youthfulness to the end of life is a universal, common desire for all humankind; however, for a long time, humans empirically could not have been spared from changes in their skin with ageing, such as sagging skin, fine wrinkles, etc. Due to a rapidly increased current concern about anti-ageing, what is more required is an external dermal agent capable of imparting firmness to the skin and lifting up sagging skin.

There has been used an external dermal agent, which contains a cosmetic film-forming agent, to impart firmness to the skin and lift up sagging skin. It is considered that such a cosmetic film-forming agent has a property of shrinking when it forms films, thereby tightening the skin and lifting up sagging skin.

Patent Literature 1 proposes a cosmetic liquid composition for maintaining the shrinking strength of film for a relatively long period of time to smooth fine wrinkles by combinationally using silica and a film forming substance such as silicon/acryl resin emulsions, sodium alginate, etc. Since such a composition contains silica, films formed therewith are relatively hard and this gives unfavorable feeling to users, when in use, as a problem.

Patent Literature 2 proposes a cosmetic for improving wrinkles by a combination use of an acryl emulsion and a water-dispersible and flexible polyurethane with a relatively low degree of shrinkage ratio. The films formed therewith, however, are problematically relatively low in contractile power, poor in adhesion to the skin, and insufficient in action of lifting up sagging skin.

PRIOR ART LITERATURES

Patent Literatures

Patent Literature 1: Japanese Patent Kokai No. 933/93
Patent Literature 2: Japanese Patent No. 4590186

DISCLOSURE OF INVENTION

Object of the Invention

The present invention has an object to provide an improved external dermal agent, which tightens the skin, lifts up sagging skin, has no stickiness to the skin, and has a satisfactory compatibility with the skin without giving any unfavorable feeling to users.

Means to Attain the Object

The present inventors energetically studied to overcome the above object and found that an improved external dermal agent, which tightens the skin, lifts up sagging skin, has no stickiness to the skin, and has favorable compatibility with the skin without giving any unfavorable feeling to users, is obtained by mixing pullulan and an alkaline-swelling polymer in a specific ratio. Thus, they accomplished the present invention.

The present invention solves the above object by providing an external dermal agent which contains pullulan and an alkaline-swelling polymer, wherein the mass ratio of the pullulan to the alkaline-swelling polymer is 10 or more.

Effects of the Invention

The external dermal agent of the present invention tightens the skin and lifts up sagging skin, resulting in improving sagging skin, fine wrinkles, etc.

BRIEF EXPLANATION OF DRAWING

FIG. 1 is a schematic diagram of lines for measurement in the face of a subject.

MODE FOR CARRYING OUT THE INVENTION

The present invention provides an external dermal agent which contains pullulan and an alkaline-swelling polymer, wherein the mass ratio of the pullulan to the alkaline-swelling polymer is 10 or more. The above-mentioned pullulan is superior in film-forming ability and is an ingredient capable of tightening the skin and lifting up sagging skin. The above-mentioned alkaline-swelling polymer is an ingredient that imparts an adequate viscosity to the external dermal agent and has an effect of reducing the stickiness of the agent. The external dermal agent of the present invention exerts distinct effects of tightening the skin, lifting up sagging skin, and having a satisfactory compatibility with the skin because it contains the above-mentioned two types of ingredients in a specific ratio.

The term "pullulan" as referred to as in the specification means a water-soluble polysaccharide having a structure of maltotriosyl units, each of which consists of three glucose molecules linked together via $\alpha$-1,4 linkage, wherein the maltotriose units are linked together via $\alpha$-1,6 linkage. Any of such pullulan can be used independently of its origin and production method, and any of those which are prepared with any methods can be used; however, suitably used are usually those which are prepared by a method of culturing a microorganism capable of producing pullulan and collecting the produced pullulan from the resulting culture. Examples of the above microorganism include those of the species *Aureobasidium pullulans*. Commercialized pullulans are advantageously used in view of their readily availability and quality; preferably used are "*Nippon Yakkyoku-Ho Pullulan*" (Pullulan, Japanese Pharmacopoeia), a product name of a pharmaceutical-grade pullulan; "Cosmetic Pullulan", a cosmetic-grade pullulan; and "Food Additive Pullulan", a food-grade pullulan, all of which are commercialized by Hayashibara Co., Ltd., Okayama, Japan.

The weight-average molecular weight and the molecular weight distribution of the above-identified pullulan should not be restricted to specific ones as long as they have a film-forming ability; however, preferably used are those which have a weight-average molecular weight in the range of, desirably, 5,000 to 1,000,000, more desirably 50,000 to 500,000, in terms of their sufficient contractile power and film flexibility.

The term "an alkaline-swelling polymer(s)" as referred to as in the specification means a polymer containing one or more members, as monomers, selected from acrylic acid, methacrylic acid, acrylic acid derivatives with hydrophobic groups, and methacrylic acid derivatives with hydrophobic groups. For example, any linear copolymers, which are formed by polymerizing two or more types of any of the above-mentioned monomers, cross polymers formed by crosslinking the above copolymers with crosslinking agents, and the like, can be used as the alkaline-swelling polymers as long as they have a property of increasing the viscosity of aqueous solutions when the pHs of the aqueous solutions are changed from acidic pHs to alkaline pHs.

Examples of the above-mentioned acrylic acid derivatives with hydrophobic groups include acrylic acid alkyl, acrylic acid ethyl hexyl, acrylic acid lauryl, acrylic acid stearyl, acrylic acid hydroxyalkyl, acrylic acid perfluorooctyl ethyl, acryl amide, alkyl acrylamide, t-butyl acrylamide, octylamide, diacetone acrylamide, etc. Examples of the above-mentioned methacrylic acid derivatives with hydrophobic groups include alkyl methacrylate, hydroxyalkyl methacrylate, methacrylic acid ethylamineoxide, dimethylaminoethyl methacrylate, butylaminoethyl methacrylate, glycidyl methacrylate, ammonium methacrylate, methacrylamide, allyl methacrylate, [tris(trimethylsilyloxy)silyl]propyl methacrylate, ethyl betaine methacrylate, propyl trimethicone methacrylate, methacrylic acid beheneth, methacrylic acid steareth, methacrylic acid methoxy PEG, etc.

Examples of the above copolymers include acrylate copolymers, alkyl acrylate copolymers, acrylates/t-butylacrylamide copolymers, acrylates/acrylamide copolymers, acrylates/C1-18 alkyl acrylate/C1-8 alkyl acrylamide copolymers, acrylates/ethylhexyl acrylate copolymers, acrylates/ethylhexyl acrylate/HEMA copolymers, acrylates/stearyl acrylate/ethylamine oxide methacrylate copolymers, acrylates/hydroxyalkyl acrylates copolymers, acrylates/lauryl acrylate/stearyl acrylate/ethylamine oxide methacrylate copolymers, acrylates/octylacrylamide copolymers, acrylates/diacetoneacrylamide copolymers, acrylates/methacrylamide copolymers, acrylates/allyl methacrylate copolymers, acrylates/C12-22 alkyl methacrylate copolymers, acrylates/ammonium methacrylate copolymers, acrylates/dimethylaminoethyl methacrylate copolymers, acrylates/2-(dimethylamino)ethyl methacrylate copolymers, acrylates/tris(trimethylsiloxy)silylpropyl methacrylate copolymers, acrylates/propyl trimethicone methacrylate copolymers, acrylates/beheneth-25 methacrylate/steareth-30 methacrylate copolymers, acrylates/methoxy PEG-23 methacrylate copolymers, acrylates/methoxy PEG-23 methacrylate/perfluorooctyl ethyl acrylate copolymers, octylacrylamide/acrylates/butylaminoethyl methacrylate copolymers, styrene/acrylates/ethylhexyl acrylate/lauryl acrylate copolymers, styrene/acrylates/ammonium methacrylate copolymers, methacryloyl ethyl betaine/acrylates copolymers, etc.

Examples of the above-mentioned crosspolymers include acrylate crosspolymers, polyacrylate crosspolymers, acrylates polyacrylate crosspolymers, acrylates/C10-30 alkyl acrylate crosspolymers, acrylates/ethylhexyl acrylate/glycidyl methacrylate crosspolymers, acrylates/steareth-20 methacrylate crosspolymers, etc. Examples of the above-mentioned crosslinking agents include aryl ethers of pentaerythritol, aryl ethers of sucrose, ethylene glycol dimethacrylates, trimethylolpropane triacrylates, etc.

Since external dermal agents are usually frequently used at around neutral pHs and those which have an adequate viscosity are readily used, in order to exert a thickening action at around neutral pHs, suitably used as the above-mentioned alkaline-swelling polymers are copolymers and/or crosspolymers, which contain one or more of acrylic acid and methacrylic acid as a monomer and one or more of acrylic acid or methacrylic acid derivatives with a hydrophobic group intramolecularly, among which acrylates/alkyl acrylate crosspolymers are more preferably used. Since these copolymers and crosspolymers contain, as a monomer, an acrylic acid derivative having a hydrophobic group intramolecularly or a methacrylic acid derivative having a hydrophobic group intramolecularly and increase the viscosity of aqueous solutions even at around neutral pHs, they are most suitably used in the external dermal agent containing pullulan according to the present invention.

The fact that the external dermal agent of the present invention has a sufficient action of lifting up sagging skin and a satisfactory compatibility with the skin, the above-identified pullulan should be used in a mass ratio of the pullulan to the above-identified alkaline-swelling polymer being in the range of 10 to 200, preferably 50 to 125. External dermal agents with the mass ratio of less than 10 are not preferable because their actions of lifting up sagging skin are not sufficient.

The external dermal agent of the present invention can be appropriately diluted or concentrated before use. Although the concentration of the above-identified pullulan to be incorporated into the external dermal agent should not specifically be restricted, the pullulan is usually incorporated into the agent for suitable use in a proportion of not more than 10% by mass, preferably 0.4 to 8% by mass, and more preferably 2 to 5% by mass to the total mass, when the agent is directly applied to the skin without any dilution or concentration.

The external dermal agent of the present invention is more preferably incorporated with a non-ionic surfactant to further improve unfavorable stickiness and compatibility with the skin. Preferable examples of the non-ionic surfactant include one or more of polyoxyethylene glycerin, polyoxyethylene glyceryl isostearate, polyglyceryl diisostearate, polyglyceryl distearate, polyglyceryl decaoleate, polyoxyethylene glyceryl triisostearate, polyglyceryl trioleate, polyoxyethyleneglyceryl tristearate, polyoxyethylene glyceryl monopyroglutamate monoisostearate, polyglyceryl heptastearate, polyglyceryl pentaisostearate, polyglyceryl pentaoleate, polyoxyethylene caprylic/capric glyceride, polyoxyethylene glyceryl monooleate, polyoxyethylene glyceryl caprylate, polyoxyethylene polyoxypropylene glyceryl ether, polyoxybutylene polyglycerol monostearyl ether, polyoxypropylene glyceryl ether, polyoxypropylene diglyceryl ether, polyoxypropylene decaglyceryl ether, polyglyceryl monoisostearate, polyglyceryl monooleate, polyoxyethylene glyceryl monostearate, polyglyceryl monostearate, polyglyceryl monolaurate, polyoxyethylene glyceryl laurate, among which polyoxyethylene glycerin is desirable.

The concentration of the above non-ionic surfactant, contained in the external dermal agent of the present invention, should not specifically be restricted as long as it does not deteriorate the desired effect and function of the present invention; however, preferably used are agents containing the non-ionic surfactant in a proportion of 0.01 to 10% by mass, desirably 0.1 to 5% by mass to the total mass.

The external dermal agent of the present invention may be usually appropriately incorporated with one or more ingredients, which are usable in conventional external dermal agents, such as humectants, oily ingredients, skin whitening agents, antioxidants, preservatives (antiseptics), chelators, ultraviolet-absorbing/scattering agents, vitamins, amino acids, pH-controlling agents, flavors, etc., by incorporating such an ingredient(s) into the external dermal agent in usual manner.

Examples of the humectants include polyalcohols such as glycerine, 1,3-propanediol, propyleneglycol, 1,3-buthanediol, dipropylene glycol, 1,2-penthanediol, isoprene glycol, pentylene glycol, polyglycerin, and polyethylene glycol;

saccharides such as erythritol, xylitol, sorbitol, maltitol, trehalose (α,α-, α,β-, or β,β-trehalose), saccharide derivatives of trehalose, dextrin, cyclodextrin, cyclic tetrasaccharides such as cyclo{→6)-α-D-glucopyranosyl-(1→3)-α-D-glucopyranosyl-(1→6)-α-D-glucopyranosyl-(1→3)-α-D-glucopyranosyl-(1→} disclosed in International Patent Publication No. 02/10361 and cyclo{→6)-α-D-glucopyranosyl-(1→4)-α-D-glucopyranosyl-(1→6)-α-D-glucopyranosyl-(1→4-α-D-glucopyranosyl-(1→} disclosed in Japanese Patent Kokai No. 2005-95148; natural moisturizing ingredients such as amino acids, sodium lactate, and sodium pyrrolidone carbonate; mucopolysaccharides and hydrolyzates thereof such as glycogen, locust bean gum, xyloglucan, quince seed, carrageenan, pectin, mannan, curdlan, succinoglucan, galactan, dermatan sulfate, keratan sulfate, chondroitin, chondroitin sulfate, mucoitin sulfate, keratosulfate, chitin, heparan sulfate, and hyaluronic acid; water-soluble polymers and salts thereof such as proteins and peptides including silk, collagen, and hydrolyzates thereof; silicons such as dimethylpolysiloxane and methylphenyl siloxane; and culture supernatants of microorganisms such as lactic acid bacteria and bifidobacteria.

Examples of the oily ingredients include plant oils and fats such as macadamia nut oil, castor oil, olive oil, cacao-seed oil, camellia oil, palm oil, Japanese wax, jojoba oil, grape seed oil, and avocado oil; animal oils and fats such as mink oil and egg-yolk oil; waxes such as bees wax, whale wax, lanolin, carnauba wax, and candelilla wax; hydrocarbons such as petrolatum, squalane, microcrystalline wax, ceresine wax, paraffin wax, and vaseline; natural and synthetic fatty acids such as capric acid, myristic acid, palmitic acid, stearic acid, behenic acid, lanolin fatty acid, linoleic acid, linolenic acid, lauric acid, myristic acid, oleic acid, and isostearic acid; natural and synthetic higher alcohols such as cetanol, stearyl alcohol, hexyldecanol, octyldodecanol, lauryl alcohol, capryl alcohol, myristyl alcohol, cetyl alcohol, cholesterol, and phytosterol; and esters such as isopropyl myristate, isopropyl palmitate, octyldodecyl myristate, and octyldodecyl oleate.

Examples of the skin-whitening agents include L-ascorbic acid and salts thereof; glycosyl ascorbic acids such as ascorbic acid-2-glucoside and salts thereof; ascorbic acid derivatives such as ascorbic acid-2-phosphate, ethyl ascorbic acid, and salts thereof; hydroquinone, its glycosides, and derivatives thereof; alkoxy salicylic acid and salts thereof; hydroquinone, its glycosides, and derivatives thereof; tranexamic acid, its derivatives, and salts thereof; resorcin derivatives; kojic acid, its derivatives, and salts thereof; ellagic acid, linoleic acid, and salts thereof; *Matricaria recutita* extract; tetrahydrocurcuminoid; and indigo extract.

Examples of the antioxidants include dibutylhydroxytoluene, butylhydroxyanisole, propyl gallate, L-ascorbic acid, vitamin E, catechins, flavonoids, and derivatives thereof.

Examples of the preservatives (antiseptics) include phenoxyethanol, benzoic acid, and salts thereof; dehydroacetic acid and salts thereof; hinokitiol, isopropyl methylphenol, benzalkonium chloride, benzethonium chloride, chlorhexidine hydrochloride, chlorhexidine gluconate, chloroxylenol, chlorphenesin, salicylic acid and salts thereof, trichlorocarbanilide, trichlorohydroxydiphenyl ether, etc.

Examples the chelators include disodium edetate, ethylenediaminetetraacetic acid salt, pyrophosphate, hexametaphosphate, citric acid, tartaric acid, gluconic acid, etc.

Examples of the ultraviolet-absorbing/scattering agents include paraaminobenzoic acid-based ultraviolet-absorbing agents, anthranilic acid-based ultraviolet-absorbing agents, salicylic acid-based ultraviolet-absorbing agents, cinnamic acid-based ultraviolet-absorbing agents, benzophenone-based ultraviolet-absorbing agents, sugar-based ultraviolet-absorbing agents, 3-(4'-methylbenzylidene)-d-camphor, 3-benzylidene-d, 1-camphor, urocanic acid, urocanic acid ethyl ester, 2-phenyl-5-methylbenzoxazole, 2,2'-hydroxy-5-methylphenylbenzotriazole, 2-(2'-hydroxy-5'-t-octylphenyl) benzotriazole, 2-(2'-hydroxy-5'-methylphenyl)benzotriazole), dibenzalazine, ziani soil methane, 4-methoxy-4'-t-butyldibenzolymethane, 5-(3,3-dimethyl-2-norbonylidene)-3-pentane-2-one, 2-hydroxy-4-methoxybenzophenone, octyldimethylparaaminobenzoate, ethylhexylparamethoxycinnamate, titanium oxide, kaolin, talc, etc.

Examples of the vitamins include vitamin A and derivatives thereof; vitamin $B_S$ including vitamin $B_1$ and derivatives thereof, vitamin $B_2$ and derivatives thereof, vitamin $B_6$ hydrochloride, vitamin $B_6$ tripalmitate, vitamin $B_6$ dioctanoate, vitamin $B_{12}$, vitamin $B_{15}$ and derivatives thereof; L-ascorbic acid and derivatives thereof; and vitamin $E_S$ including α-tocopherol, β-tocopherol, γ-tocopherol, and vitamin E acetate; vitamin $D_S$; vitamin H; pantothenic acid; pantethine, vitamin F; vitamin K; vitamin P and derivatives thereof; and vitamin U, ferulic acid, γ-oryzanol, α-lipoic acid, orotic acid, coenzyme Q10, and derivatives thereof, as well as salts thereof.

Examples of the amino acids include glycine, alanine, valine, leucine, isoleucine, serine, threonine, phenylalanine, tyrosine, asparagine, glutamine, taurine, tryptophan, cystine, cysteine, methionine, proline, hydroxyproline, asparaginic acid, glutamic acid, arginine, histidine, lysine, carnitine, citrulline, and derivatives thereof, as well as salts thereof.

Examples of the pH-controlling agents include sodium hydroxide, potassium hydroxide, triethanolamine, nitrilotriethanol, citric acid, sodium citrate, potassium dihydrogenphosphate, disodium hydrogenphosphate, boric acid, and borax.

Examples of the flavors include benzaldehyde, benzyl benzoate, phenylacetate, Sandalore (a synthetic sandalwood odorant), eugenol, lilial, lyral, linalool, 2-methyl-3-(4-methylphenyl)-propanal, musk ketone, cinnamicaldehyde, belt fix, methylionone, geranyl formate, iso-E-super, γ-undecalactone, hexylsalicylate, cis-3-hexenyl salicylate, methyl dihydrojasmonate, tetrahydrofuryl 3-mercaptopropionate, kobanoru, vanillin, baniraru, geranium oil, pennyroyal oil, birch oil, and almoize oil.

The external dermal agent of the present invention should not specifically be restricted to a specific form; it can be prepared into various forms of aqueous solution, solubilized, emulsified, dispersed, water/oil biphasic, oil/water/powder triphasic, oil-in-water emulsion, and water-in-oil emulsion systems.

Since the external dermal agent of the present invention tightens the skin and lifts up sagging skin to improve sagging skin and fine wrinkles, it can be suitably used as an external dermal agent having an action of lifting up the skin of the face, neck, arm, abdomen, breech, leg, etc.; and more preferably it can be used as an external dermal agent having an action of lifting up the skin of the face.

The present invention is explained in more detail with reference to the following experiments:

Experiment 1: Effect of the Mass Ratio of Pullulan to Alkaline-Swelling Polymer

Several samples were prepared and subjected to a sensory test to examine the effect of the mass ratio of a pullulan to an alkaline-swelling polymer on their induced skin-firmness and compatibility with the skin, as well as twisting of films formed therewith.

Test samples 1 to 5 and a control sample were prepared by mixing "COSMETIC PULLULAN", a product name of a pullulan with a weight-average molecular weight of 200,000, commercialized by Hayashibara Co., Ltd., Okayama, Japan; "Pemulen TR-2", an acrylates/C10-30 alkyl acrylate crosspolymer as an alkaline-swelling polymer, commercialized by The Lubrizol Corporation, Ohio, USA; sodium hydroxide for neutralization; and refined water in the mass ratios as listed in Table 1.

The sensory test was conducted with a panel consisting of nine healthy males and females, 33 to 50 years old: Each panelist was applied with 0.2 mL of any one of the test samples 1 to 5 and the control sample at their antebrachial regions and then immediately evaluated on their feelings of skin firmness and compatibility of the samples with their skins, and twisting of films formed with the samples, based on the following criteria. The results are in Table 1.

About skin firmness:
⊚: There were 7 to 9 panelists who answered that they felt a satisfactory skin-firmness.
○: There were 5 to 6 panelists who answered that they felt a satisfactory skin-firmness.
Δ: There were 3 to 4 panelists who answered that that they felt a satisfactory skin-firmness.
X: There were 0 to 2 panelists who answered that that they felt a satisfactory skin-firmness.

About compatibility with the skin:
⊚: There were 7 to 9 panelists who answered that they felt a satisfactory compatibility with the skin.
○: There were 5 to 6 panelists who answered that they felt a satisfactory compatibility with the skin.
Δ: There were 3 to 4 panelists who answered that they felt a satisfactory compatibility with the skin.
X: There were 0 to 2 panelists who answered that they felt a satisfactory compatibility with the skin.

About twisting of film:
⊚: There were 7 to 9 panelists who answered that they felt no twisting of a film formed with any one of the samples.
○: There were 5 to 6 panelists who answered that they felt no twisting of a film formed with any one of the samples.
Δ: There were 3 to 4 panelists who answered that they felt no twisting of a film formed with any one of the samples.
X: There were 0 to 2 panelists who answered that they felt no twisting of a film formed with any one of the samples.

TABLE 1

| | Ingredient | Test sample 1 (% by mass) | Test sample 2 (% by mass) | Test sample 3 (% by mass) | Test sample 4 (% by mass) | Test sample 5 (% by mass) | Control sample (% by mass) |
|---|---|---|---|---|---|---|---|
| (A) | Pullulan (weight-average molecular weight of 200,000) | 0.2 | 0.4 | 2 | 5 | 8 | 0 |
| (B) | Acrylates/C10-30 alkyl acrylate crosspolymer | 0.04 | 0.04 | 0.04 | 0.04 | 0.04 | 0.04 |
| | Sodium hydroxide | 0.009 | 0.009 | 0.009 | 0.009 | 0.009 | 0.009 |
| | Refined water | 99.751 | 99.551 | 97.951 | 94.951 | 91.951 | 99.951 |
| | Total | 100 | 100 | 100 | 100 | 100 | 100 |
| | (A)/(B) | 5 | 10 | 50 | 125 | 200 | 0 |
| Evaluation | Skin firmness | X | Δ | ○ | ⊚ | ⊚ | X |
| | Compatibility with the skin | Δ | ○ | ⊚ | ○ | ○ | Δ |
| | Twisting of film | ⊚ | ⊚ | ⊚ | ○ | X | ⊚ |

As clear from Table 1, the test sample 1, which has the mass ratio of the pullulan to the acrylates/C10-30 alkyl acrylate crosspolymer being 5, had no effect of imparting firmness to the skin similarly as in the control sample; while the test samples 2 to 5 with the mass ratios ranging from 10 to 200 were superior in the effects to the test sample 1 and the control sample, among which the test samples 4 and 5 with the mass ratios of 125 and 200, respectively, were particularly superior in the effects. The test samples 2 to 5 with the mass ratios ranging from 10 to 200 were superior in compatibility with the skin to the test sample 1 and the control sample, among which the test sample 3 with the mass ratio of 50 was distinctly superior in compatibility with the skin. The control sample and the test samples 1 to 4 with the mass ratios ranging from 0 to 125 gave almost no twisting of a film formed with any one of the test samples, while twisting of film was observed in the test sample 5 with the mass ratio of 200.

The above results indicate that the external dermal agents, which have a mass ratio of pullulan to an alkaline-swelling polymer being at least 10 and preferably in the range of 10 to 200, are superior in skin firmness and compatibility with the skin, and those which have a mass ratio of pullulan to an alkaline-swelling polymer being in the range of 50 to 125 are particularly superior in skin firmness and compatibility with the skin, and are substantially free of twisting of film.

The test samples 1 to 5 were substantially free of any particular inconvenience when applied to the antebrachial regions of the panelists and in the sensory test after the applications; however, an external dermal agent, alternatively prepared with only 5% by mass of pullulan and refined water, was too sticky to conduct the prescribed sensory test. This result shows that the incorporation of any one of the prescribed alkaline-swelling polymers to pullulan inhibits the stickiness inherent to pullulan.

Experiment 2: Evaluation of the Action of Lifting Up Sagging Skin>

External dermal agents as test samples were prepared and evaluated on their actions of lifting up sagging skin, based on the result of the test sample 4 which had been determined in Experiment 1 to have a distinct effect of imparting firmness to the skin, a satisfactory compatibility with the skin, and a lesser generation of twisting of films formed with the test sample 4.

The materials in Table 2 were mixed in the ratios shown in Table 2 to prepare external dermal agents as a test sample and an external dermal agent as a control sample similarly as in the test sample, but free of pullulan. Twenty healthy females, 35 to 70 years old, who had sagging skin and reduced skin-firmness, were applied with the test sample at the right half of each subject's face and with the control sample at the left half of each subject's face, respectively. The subjects were photographed their faces from directly in front with a 12.3 megapixels digital single-lens reflex camera, followed by measuring both the lengths of the lines between the hairline and the jaw of each subject, passing through the corners of each subject's eyes in parallel with the center line of each subject's face (corresponding to Lines 1 and 4 in FIG. 1), and the lengths of the lines between the hairline and the jaw of each subject, passing through the inner corners of each subject's eyes in parallel with the center line of each subject's face (corresponding to Lines 2 and 3 in FIG. 1), and determining variations based on the difference between the determined lengths and their corresponding values before conducting this experiment. Average values for each of the measured values and the variations are in Table 3. The values measured before the applications and at 30 and 60 min after the applications were examined with Student's paired t-test, and any of which has a level of significance of 5% or lower is judged to have a significant difference and expressed with the symbol "*" in the table. The variations of the external dermal agents of the test sample and the control sample were respectively examined with the same t-test as used in the above, resulting in that those with a level of significance of 5% or lower were judged to have a significant difference and are expressed with the symbol "**" in the table.

TABLE 2

| Ingredient | "Product name" (Sales company) | External dermal agent as a test sample (% by mass) | External dermal agent as a control sample (% by mass) |
|---|---|---|---|
| Pullulan with a weight-average molecular weight of 200,000 | "Cosmetic Pullulan", (Hayashibara Co., Ltd., Okayama, Japan) | 5 | 0 |
| Acrylates/C10-30 alkyl acrylate crosspolymer | "Carbopol Ultrez 20", (Gattefossé, KS, USA) | 0.04 | 0.04 |
| Polyoxyethylene glycerin (26 E.O.) | "Liponic EG-1", (Vantage Specialty Ingredients, NJ, USA; formerly Lipo Chemicals) | 0.3 | 0.3 |
| Penthyleneglycol | "Hydrolite-5", (Safic-Alcan, Puteaux, France | 0.5 | 0.5 |
| Phenoxyethanol | "Phenoxetol", (Clariant SE, Muttenz, Switzerland) | 0.8 | 0.8 |
| Chlorphenesin | "Chlorphenesin BP 73", (Azelis Corporate Services NV Berchem, Belgium) | 0.28 | 0.28 |
| Sodium hydroxide | | 0.009 | 0.009 |
| Refined water | | 93.071 | 98.071 |
| Total | | 100 | 100 |

TABLE 3

| | | Before application | | Thirty minutes after application | | Sixty minutes after application | |
|---|---|---|---|---|---|---|---|
| | | Line length passing through the corner of an eye (mm) | Line length passing through the inner corner of an eye (mm) | Line length passing through the corner of an eye (mm) | Line length passing through the inner corner of an eye (mm) | Line length passing through the corner of an eye (mm) | Line length passing through the inner corner of an eye (mm) |
| Measured value | External dermal agent as a test sample | 151.03 | 171.57 | 150.06* | 170.53* | 150.37* | 170.80* |
| | External dermal agent as a control sample | 149.26 | 170.79 | 149.24 | 170.79 | 149.22 | 170.77 |

TABLE 3-continued

|  |  | Before application | | Thirty minutes after application | | Sixty minutes after application | |
| --- | --- | --- | --- | --- | --- | --- | --- |
|  |  | Line length passing through the corner of an eye (mm) | Line length passing through the inner corner of an eye (mm) | Line length passing through the corner of an eye (mm) | Line length passing through the inner corner of an eye (mm) | Line length passing through the corner of an eye (mm) | Line length passing through the inner corner of an eye (mm) |
| Variation from before application | External dermal agent as a test sample |  |  | −0.97** | −1.04** | −0.66** | −0.77** |
|  | External dermal agent as a control sample |  |  | −0.02 | 0.00 | −0.04 | −0.02 |

As clear from Table 3, there was observed no change in the perpendicular line passing through the corner or the inner corner of an eye of each subject applied with the external dermal agent as a control sample, while the line passing through the corner or the inner corner of an eye of each subject applied with the external dermal agent as a test sample at 30 min after the application became shorter than that before the application by 0.97 to 1.04 mm, while even at 60 min after the application, it became shorter than that before the application by 0.66 to 0.77 mm, indicating that the test sample maintained the effect of lifting up the skin of the face as an effect of lifting up sagging skin. These results indicate that the external dermal agent, containing pullulan and an alkaline-swelling polymer in a prescribed ratio, has an effect of lifting up sagging skin to distinctly improve sagging skin.

The following Examples explain the present invention in more detail, but they should never restrict the present invention.

Example 1

External Dermal Agent

| Ingredient | (% by mass) |
| --- | --- |
| (1) "Cosmetic Pullulan", a product name of a cosmetic-grade pullulan with a weight-average molecular weight of 200,000 commercialized by Hayashibara Co., Ltd., Okayama, Japan | 5.0 |
| (2) AMP-Acrylates polyacrylate crosspolymer | 0.1 |
| (3) Polyoxyethylene glycerin (26 E.O.) | 0.3 |
| (4) "AA2G", a product name of ascorbic acid 2-glucoside commercialized by Hayashibara Co., Ltd., Okayama, Japan | 1.0 |
| (5) Pentylene glycol | 0.5 |
| (6) Citric acid | q.s. |
| (7) Sodium citrate | q.s. |
| (8) Sodium hydroxide | q.s. |
| (9) Refined water | Balance |

The product is a superior external dermal agent which tightens the skin, lifts up sagging skin, has no stickiness to the skin, and has a satisfactory compatibility with the skin, without giving any unfavorable feeling to users.

Example 2

External Dermal Agent

| Ingredient | (% by mass) |
| --- | --- |
| (1) "Cosmetic Pullulan", a product name of a cosmetic-grade pullulan with a weight-average molecular weight of 200,000 commercialized by Hayashibara Co., Ltd., Okayama, Japan | 4.0 |
| (2) Acrylates/ethylhexyl acrylate copolymer | 0.05 |
| (3) Polyoxypropylene glyceryl ether | 0.3 |
| (4) "AA2G", a product name of ascorbic acid 2-glucoside commercialized by Hayashibara Co., Ltd., Okayama, Japan | 1.0 |
| (5) 1,3-Buthanediol | 0.5 |
| (6) Citric acid | q.s. |
| (7) Sodium citrate | q.s. |
| (8) Sodium hydroxide | q.s. |
| (9) Refined water | Balance |

The product is a superior external dermal agent which tightens the skin, lifts up sagging skin, has no stickiness to the skin, and has a satisfactory compatibility with the skin, without giving no unfavorable feeling to users.

Example 3

External Dermal Agent

| Ingredient | (% by mass) |
| --- | --- |
| (1) "Cosmetic Pullulan", a product name of a cosmetic-grade pullulan with a weight-average molecular weight of 200,000 commercialized by Hayashibara Co., Ltd., Okayama, Japan | 2.0 |
| (2) Acrylates/alkyl methacrylate (C12-22) copolymer | 0.02 |
| (3) Polyoxyethylene polyoxypropylene glyceryl ether (24 E.O.) (24 P.O.) | 0.3 |
| (4) "AA2G", a product name of ascorbic acid 2-glucoside commercialized by Hayashibara Co., Ltd., Okayama, Japan | 1.0 |
| (5) 1,3-Propanediol | 0.5 |
| (6) Squalane | 0.5 |
| (7) Citric acid | q.s. |
| (8) Sodium citrate | q.s. |
| (9) Sodium hydroxide | q.s. |
| (10) Refined water | Balance |

Explanation of Symbols

1: A line passing through the corner of the right eye of a subject and running in parallel with the center line of the subject's face.
2: A line passing through the inner corner of the right eye of a subject and running in parallel with the center line of the subject's face.
3: A line passing through the inner corner of the left eye of a subject and running in parallel with the center line of the subject's face.
4: A line passing through the corner of the left eye of a subject and running in parallel with the center line of the subject's face.

The invention claimed is:

1. An external dermal agent, which comprises pullulan and an alkaline-swelling polymer as the only active ingredients to lift up the skin of the face, wherein said pullulan is in an amount of 2 to 5% by mass to the total mass of the external dermal agent, and the mass ratio of said pullulan to said alkaline-swelling polymer is in the range of 50 to 125.

2. The external dermal agent of claim 1, wherein said alkaline-swelling polymer is one or more members selected from the group consisting of acrylic acid and methacrylic acid as a monomer, or a copolymer and/or a crosspolymer comprising one or more members selected from the group consisting of an acrylic acid derivative having a hydrophobic group intramolecularly and a methacrylic acid derivative having a hydrophobic group intramolecularly.

3. The external dermal agent of claim 1, wherein said alkaline-swelling polymer is an acrylates/alkyl acrylate crosspolymer.

4. The external dermal agent of claim 1, which further contains a non-ionic surfactant.

5. The external dermal agent of claim 4, wherein said non-ionic surfactant is a polyoxyethylene glycerin.

6. A method for lifting up sagging skin of a subject in need thereof, which comprises a step of applying an external dermal agent comprising pullulan and an alkaline-swelling polymer as the only active ingredients to lift up the skin of the face, wherein said pullulan is in an amount of 2 to 5% by mass to the total mass of the external dermal agent, and the mass ratio of said pullulan to said alkaline-swelling polymer is in the range of 50 to 125.

7. The method of claim 6, wherein said alkaline-swelling polymer is one or more members selected from the group consisting of acrylic acid and methacrylic acid as a monomer, or a copolymer and/or a crosspolymer comprising one or more members selected from the group consisting of an acrylic acid derivative having a hydrophobic group intramolecularly and a methacrylic acid derivative having a hydrophobic group intramolecularly.

8. The method of claim 6, wherein said alkaline-swelling polymer is an acrylates/alkyl acrylate crosspolymer.

9. The method of claim 6, wherein said external dermal agent further contains a non-ionic surfactant.

10. The method of claim 9, wherein said non-ionic surfactant is a polyoxyethylene glycerin.

* * * * *